(12) United States Patent
Spadini et al.

(10) Patent No.: US 7,846,462 B2
(45) Date of Patent: Dec. 7, 2010

(54) PERSONAL CARE IMPLEMENT CONTAINING A STABLE REACTIVE SKIN CARE AND CLEANSING COMPOSITION

(75) Inventors: Alessandro Luigi Spadini, Stamford, CT (US); Melissa Iva Katz, Weston, CT (US); David Robert Williams, Monroe, CT (US); Marcina Siciliano, New Haven, CT (US); Gregory Aaron Grissett, Milford, CT (US); Evan Hillman, Torrington, CT (US); Andre Puleo, Bethany, CT (US); Megan Kathleen Hurley, Middletown, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 1110 days.

(21) Appl. No.: 10/742,984

(22) Filed: Dec. 22, 2003

(65) Prior Publication Data

US 2005/0136098 A1 Jun. 23, 2005

(51) Int. Cl.
A01N 25/34 (2006.01)
(52) U.S. Cl. .................. 424/402; 424/401; 424/43; 424/44; 424/46; 510/141
(58) Field of Classification Search .............. 424/402, 424/401, 43, 44, 46; 510/141
See application file for complete search history.

(56) References Cited

U.S. PATENT DOCUMENTS

| | | | |
|---|---|---|---|
| 3,194,736 A | | 7/1965 | Braun et al. |
| 3,866,800 A | | 2/1975 | Schmitt et al. |
| 4,372,867 A | * | 2/1983 | Taragos ................. 15/104.93 |
| 4,789,262 A | * | 12/1988 | Sanchez ................. 401/201 |
| 4,987,632 A | * | 1/1991 | Rowe et al. ............ 15/104.93 |
| 5,147,576 A | * | 9/1992 | Montague et al. ......... 510/417 |
| 5,958,454 A | * | 9/1999 | Schrempf et al. .......... 424/466 |
| 6,063,390 A | * | 5/2000 | Farrell et al. ............. 424/404 |
| 6,274,127 B1 | | 8/2001 | Schraer et al. |
| 6,290,943 B1 | | 9/2001 | Naser et al. |
| 6,310,014 B1 | | 10/2001 | Rau |
| 6,451,327 B1 | | 9/2002 | Nakagaki et al. |
| 6,569,415 B1 | | 5/2003 | Orloff et al. |
| 6,630,438 B1 | * | 10/2003 | Arnau et al. ............. 510/439 |
| 7,008,620 B2 | * | 3/2006 | Sun et al. ................. 424/73 |
| 2002/0192173 A1 | | 12/2002 | Glenn, Jr. et al. |
| 2002/0193256 A1 | | 12/2002 | Harris et al. |
| 2003/0108506 A1 | | 6/2003 | Scholz et al. |

FOREIGN PATENT DOCUMENTS

| | | |
|---|---|---|
| EP | 0 897 719 | 2/1999 |
| GB | 2 242 358 | 10/1991 |
| GB | 2 252 358 | 10/1991 |
| GB | 2 386 604 | 9/2003 |
| WO | 97/40814 | 11/1997 |
| WO | 01/08657 | 2/2001 |
| WO | 02/02730 | 1/2002 |
| WO | 02/069917 | 9/2002 |
| WO | 02/069917 A2 | 9/2002 |
| WO | 02/069917 A3 | 9/2002 |
| WO | 03/070211 | 8/2003 |
| WO | 2004/058214 | 7/2004 |

OTHER PUBLICATIONS

ChemBrief, "Optigel SH Synthetic Silicate", Jun. 2003, Southern Clay Products, Inc., vol. 3, Iss. 2.*
The Condensed Chemical Dictionary, 1971, Van Nostrand Reinhold Co., (8th ed. by Gessner Hawley), p. 674, "Phase" (2).*
PCT Search Report PCT/EP2004/013789, mailed May 9, 2005, 4 pp.
Spadini, et al., U.S. Appl. No. 10/730,218, filed Dec. 8, 2003, For: Stable Nonaqueous Reactive Skin Care and Cleansing Composition Having a Continuous and Discontinuous Phase.
Spadini, et al., U.S. Appl. No. 10/730,709, filed Dec. 8, 2003, For: Stable Liquid Reactive Skin Care and Cleansing Packaged Product.
PCT Search Report, PCT/EP2004/013789, mailed May 9, 2005, 4 pp.

* cited by examiner

*Primary Examiner*—Gina C Yu
(74) *Attorney, Agent, or Firm*—Alan A. Bornstein

(57) ABSTRACT

Skin care or cleansing implements are described containing a liquid, semi-solid or solid cleansing or skin treatment composition that is releasably associated with the implement. The composition is substantially nonaqueous and has a continuous and a discontinuous phase. Components of the discontinuous phase can react with each other or with water when water is blended with the nonaqueous cleansing or skin treatment composition during consumer use. Methods for treating the skin with the inventive implements are also described.

21 Claims, No Drawings

PERSONAL CARE IMPLEMENT CONTAINING A STABLE REACTIVE SKIN CARE AND CLEANSING COMPOSITION

BACKGROUND

1. Field of the Invention

The present invention relates to a personal skin care and cleansing implement containing a stable reactive skin care and cleansing composition.

2. Background of the Invention

Implements are frequently used to efficiently apply skin care and cleansing compositions and have included woven and nonwoven wipes, polymeric mesh bags and sponges to name a few widely used forms of implements. Consumers also desire to better visualize the effects of the cleansing and skin treatment. Prior art implements provided a signal for the simple depletion of a colored active substance via a decrease in color intensity as the active substance concentration in the implement decreased as a function of use. For example, U.S. Pat. No. 4,987,632 titled Wiping Article, issued to Rowe et al. on Jan. 29, 1991 discloses a substantially dry-to-the-touch wiping article which is suitable for use in cleaning soiled surfaces in the presence of water, and that has a water absorbent substrate impregnated with a detergent active compound and sandwiched by a moisture barrier. The detergent active material or the moisture barrier can comprise a water-soluble dyestuff or colorant, the disappearance of which can signal exhaustion of the material.

Reactive systems have also been utilized to measure the change in concentration in an active substance. For example, U.S. Pat. No. 4,678,704 titled Impregnated Substrate Incorporating An Indicator Dye issued to A. Fellows on Jul. 1, 1987 discloses an impregnated fabric material that has been bonded to an active cationic impregnant, and an anionic indicator dye in combination with a further cationic component also applied to the fabric material, wherein the dye bonds to the second cationic component more readily than to the fabric The second cationic component competes with the impregnant for bonding to the dye. In the case of a wiping cloth, the dye acts as an indicator the disappearance of which indicates depletion of the active component with use.

The use of a porous or netted bag or pouch to carry soap is known. The prior art includes U.S. Pat. No. 1,682,119 where a bag is provided with soap in a flake or fragment form. Similarly U.S. Pat. No. 2,607,940 discloses a mesh bag so that a soap can be easily inserted. Similar arrangements are taught in e.g. U.S. Pat. No. 3,167,805, U.S. Pat. No. 4,190,550, U.S. Pat. No. 4,228,834, U.S. Pat. No. 4,480,939, and U.S. Pat. No. 5,462,378. U.S. Pat. No. 4,789,262 teaches a soap holding cleaning pad. U.S. Pat. No. 5,839,842 discloses a cleansing system with a toilet bar and a sponge in a porous pouch. U.S. Pat. No. 6,042,288 teaches the use of a synthetic detergent bar and a pouf for holding the bar. JP Patent No. 10137152 also teaches a solid soap in an expansible net. However, the problem with prior art skin and hair care and cleansing implements is the lack of a system where a reaction between two components of the skin care and cleansing composition contained or absorbed by the implement or a reaction of one of its components and water can take place to cause a noticeable change for the consumer and that is optionally accompanied by one or more skin or hair benefits.

Surprisingly it has been found that a skin care and cleansing implement can be made having a skin care or cleansing composition releasably associated with the implement, where the composition may either be coated onto or held within internal pores of the implement, held within a pouch associated with the implement capable of dispensing a desired amount or where a portion of the pouch can dissolve or disintegrate and release the composition contained within it. The inventive composition has one or more reactive components that react either with each other or with water when water is added. This reaction may signify to the consumer that the skin care or cleansing composition releasably associated with the implement has been activated and is ready for further use. The reaction can be signified via a change in color, production of a gas (e.g. effervescence), activation of a warming or a cooling effect on the skin or another noticeable change in a physical property or appearance of the implement may occur. The lessening of the intensity of the color, effervescence, warming or cooling, etc. will signify to the consumer the transfer of the active or cleansing components to the skin and hair and ultimately the depletion of the activity of the implement.

SUMMARY OF THE INVENTION

In one aspect of the invention is a personal care implement, including but not limited to:
a. a water insoluble substrate, the substrate affixed to a membrane barrier;
b. the membrane barrier being water soluble or dispersible and defining a chamber;
c. the chamber containing a composition including a dispersed phase and a continuous phase;
d. the dispersed phase including a first component, the first component being capable of chemically reacting with a second component that is different from the first;
e. the continuous phase present in the composition is composed of a substantially anhydrous carrier;
f. at least one stabilizer contained in the dispersed phase wherein the stabilizer is selected from an organophilic particle, an amphipathic compound or polymer, or a crystalline hydroxyl containing stabilizer;
g. wherein the first component is substantially unsolvated in the carrier; and
h. an anionic surfactant in a concentration of at least about 2% by wt. based on the composition when the at least one stabilizer consists solely of waxy particles, amphipathic compounds or polymers, or a combination thereof.

In a further aspect of the invention is a method of treating the skin or hair, comprising the steps of:
a. adding water to the implement described above;
b. allowing the membrane to sufficiently dissolve or disperse in order to transfer a substantial portion of the composition contained in the chamber to the water insoluble substrate;
c. contacting the skin or hair with the implement and the transferred composition;
d. rubbing the skin or hair with the implement and the transferred composition; and
e. rinsing off the composition from the skin.

In another aspect of the invention is a skin care or cleansing implement, including but not limited to:
a. a water insoluble substrate;
b. a composition including a dispersed phase and a continuous phase, wherein the composition is releasably associated with the substrate;
c. the dispersed phase including a first component, the first component being capable of chemically reacting with a second component that is different from the first;
d. the continuous phase present in the composition being composed of a substantially anhydrous carrier;

e. at least one stabilizer contained in the dispersed phase wherein the stabilizer is selected from an organophilic particle, an amphipathic compound or polymer, or a crystalline hydroxyl containing stabilizer;
f. wherein the first component is substantially unsolvated in the carrier; and
g. an anionic surfactant in a concentration of at least about 2% by wt. based on the composition when the at least one stabilizer consists solely of waxy particles, amphipathic compounds or polymers, or a combination thereof.

In another aspect of the invention is a method of treating the skin or hair, including but not limited to the steps of:
a. adding water to the implement described above;
b. contacting the skin or hair with the implement;
c. rubbing the skin or hair with the implement until a substantial portion of the composition is transferred to the skin or hair; and
d. rinsing off the composition.

In another aspect of the invention is a skin care or cleansing implement, including but not limited to:
a. a water insoluble substrate composed of a filamentous or spongeform body;
b. a dispensing device having an orifice, a wall and defining a chamber; wherein the device is adjacent to the substrate, wherein the wall is composed of a water insoluble material;
c. a composition including a dispersed phase and a continuous phase contained in the chamber;
d. the dispersed phase including a first component, the first component being capable of chemically reacting with a second component that is different from the first;
e. the continuous phase present in the composition being composed of a substantially anhydrous carrier;
f. at least one stabilizer contained in the dispersed phase wherein the stabilizer is selected from an organophilic particle, an amphipathic compound or polymer, or a crystalline hydroxyl containing stabilizer;
g. wherein the first component is substantially unsolvated in the carrier; and
h. an anionic surfactant in a concentration of at least 2% by wt. based on the composition when the at least one stabilizer consists solely of waxy particles, amphipathic compounds or polymers, or a combination thereof.

In another aspect of the invention is a method of treating the skin or hair, including but not limited to the steps performed in no particular sequence of:
a. dispensing the composition onto the substrate of the implement described above;
b. adding water to the implement;
c. contacting the skin or hair with the implement;
d. rubbing the skin or hair with the implement until a substantial portion of the composition is transferred to the skin or hair (preferably greater than about 50% by wt. of the composition); and
e. rinsing off the composition.

DETAILED DESCRIPTION OF THE INVENTION

In one aspect of the invention is a personal care implement, including but not limited to:
a. a water insoluble substrate (preferably having at least one woven or non-woven fabric layer), the substrate affixed to a membrane barrier;
b. the membrane barrier being water soluble or dispersible and defining a chamber;
c. the chamber containing a composition including a dispersed phase and a continuous phase;
d. the dispersed phase including a first component, the first component being capable of chemically reacting with a second component that is different from the first;
e. the continuous phase present in the composition is composed of a substantially anhydrous carrier;
f. at least one stabilizer contained in the dispersed phase wherein the stabilizer is selected from an organophilic particle, an amphipathic compound or polymer, or a crystalline hydroxyl containing stabilizer;
g. wherein the first component is substantially unsolvated in the carrier; and
h. an anionic surfactant in a concentration of at least about 2% by wt. based on the composition when the at least one stabilizer consists solely of waxy particles, amphipathic compounds or polymers, or a combination thereof.

Advantageously the dispersed phase comprises the first and the second components and wherein the second component is substantially unsolvated in the carrier. Preferable the reaction of the first component with water or the first component and the second component is not polymerization. More preferably the at least one reactive component has a particle size range of about 0.5 to 5000μ. Most preferably the stabilizer is an organophilic particle in the particle size range of about 0.02 to 250μ. Advantageously the stabilizer is selected from a waxy particle, organophilic silica, organophilic clay, or blends thereof. The stabilizer may also be an amphipathic compound or polymer with some oil soluble groups substantially solvated by the carrier and some polar groups substantially unsolvated by the carrier. Advantageously the stabilizer is an amphipathic polymer selected from polysiloxanes, polyalkylene ethers, polysaccharides, polyacrylates, or polystyrene each substituted with at least one linear or branched C8 to C24 alkyl or alkenyl chain.

In a preferred embodiment the carrier of the inventive implement may contain components that are polar, nonpolar or a blend thereof. Advantageously the first and second components do not substantially react with each other until dispersed or dissolved in water. The implement may further include dispersed surfactants that are substantially unsolvated by the carrier. In a preferred embodiment the implement may further include structuring agents that form lamellar, hexagonal, or cubic surfactant phases upon contact with water at 25 C.

Advantageously the first component in one embodiment is capable of producing a gas in aqueous solution when reacted with an acid and the second component is an acid or forms an acid in the presence of water. In another embodiment the first component is capable of generating a peroxide compound when dissolved in water. In a further embodiment the first component is capable of generating sulfide ions when reacted with an alkaline material and water.

Preferably the carrier contains an oil, an emulsifier and wherein the stabilizer is an organophilic clay; and the composition contains a total of at least about 10% of reactive dispersed solids by wt based on the composition and the first component is a solid or semisolid containing dissolved carbon dioxide in a preferred embodiment.

In a preferred embodiment, the at least one layer of the woven or non-woven fabric comprises a hydrophilic fabric. Advantageously the hydrophilic fabric is a blend of cellulosic and non-cellulosic fibers. Preferably the hydrophilic fabric comprises rayon and polyester. More preferably the hydrophilic fabric comprises rayon and polyester in the concentration ratio range of about 10:90 to 90:10. Most preferably the hydrophilic fabric contains a plurality of apertures having a major axis diameter in the range of about 0.5 to 10 mm and wherein the apertures are distributed on the substrate in the range of about 1 to 10 per linear centimeter. Advantageously the hydrophilic fabric comprises at least one layer of fibers made by a process selected from hydroentangled, wet laid, dry laid, spun bonded, needle punched, or air laid.

In a further aspect of the invention is a method of treating the skin or hair, comprising the steps of:
  a. adding water to the implement described above;
  b. allowing the membrane to sufficiently dissolve or disperse in order to transfer a substantial portion of the composition contained in the chamber to the water insoluble substrate;
  c. contacting the skin or hair with the implement and the transferred composition;
  d. rubbing the skin or hair with the implement and the transferred composition; and
  e. rinsing off the composition from the skin.

In another aspect of the invention is a skin care or cleansing implement, including but not limited to:
  a. a water insoluble substrate (preferably having at least one woven or non-woven fabric layer);
  b. a composition including a dispersed phase and a continuous phase, wherein the composition is releasably associated with the substrate;
  c. the dispersed phase including a first component, the first component being capable of chemically reacting with a second component that is different from the first;
  d. the continuous phase present in the composition being composed of a substantially anhydrous carrier;
  e. at least one stabilizer contained in the dispersed phase wherein the stabilizer is selected from an organophilic particle, an amphipathic compound or polymer, or a crystalline hydroxyl containing stabilizer;
  f. wherein the first component is substantially unsolvated in the carrier; and
  g. an anionic surfactant in a concentration of at least about 2% by wt. based on the composition when the at least one stabilizer consists solely of waxy particles, amphipathic compounds or polymers, or a combination thereof.

Preferably the composition is releasably associated with the substrate by a mechanism selected from surface coating of fibers or filaments in at least a portion of the substrate, absorption into pores or pockets contained in at least a portion of the substrate, or a combination thereof. Advantageously the concentration of the composition is greater than about 1, 2, 3, 5, 7, 10, 11, 15, 17, 20, 21, 25 or 30% by wt. of the substrate. More preferably the concentration of the composition is greater than about 7.5% by wt. based on the substrate.

In another aspect of the invention is a method of treating the skin or hair, including but not limited to the steps of:
  a. adding water to the implement described above;
  b. contacting the skin or hair with the implement;
  c. rubbing the skin or hair with the implement until a substantial portion of the composition is transferred to the skin or hair; and
  d. rinsing off the composition.

In a further aspect of the invention is a skin care or cleansing implement, including but not limited to:
  a. a water insoluble substrate composed of a filamentous or spongeform body (preferably having at least one woven or non-woven fabric layer);
  b. a dispensing device having an orifice, a wall and defining a chamber; wherein the device is adjacent to the substrate, wherein the wall is composed of a water insoluble material;
  c. a composition including a dispersed phase and a continuous phase contained in the chamber;
  d. the dispersed phase including a first component, the first component being capable of chemically reacting with a second component that is different from the first;
  e. the continuous phase present in the composition being composed of a substantially anhydrous carrier;
  f. at least one stabilizer contained in the dispersed phase wherein the stabilizer is selected from an organophilic particle, an amphipathic compound or polymer, or a crystalline hydroxyl containing stabilizer;
  g. wherein the first component is substantially unsolvated in the carrier; and
  h. an anionic surfactant in a concentration of at least 2% by wt. based on the composition when the at least one stabilizer consists solely of waxy particles, amphipathic compounds or polymers, or a combination thereof.

Advantageously the concentration of the composition is greater than about 1, 2, 3, 5, 7, 10, 11, 15, 17, 20, 21, 25 or 30% by wt. of the substrate. Preferably the concentration of the composition is greater than 7.5% by wt. of the substrate. Preferably the wall is made of a material selected from polyethylene, polypropylene, PET, or a combination thereof. More preferably the orifice is selected from a duck bill valve or clean cut-off dispensing valves.

In another aspect of the invention is a method of treating the skin or hair, including but not limited to the steps performed in no particular sequence of:
  a. dispensing the composition onto the substrate of the implement described above;
  b. adding water to the implement;
  c. contacting the skin or hair with the implement;
  d. rubbing the skin or hair with the implement until a substantial portion of the composition is transferred to the skin or hair (preferably greater than about 50% by wt. of the composition); and
  e. rinsing off the composition.

Implement Substrates

The inventive implement may be formed of any porous or water permeable material sufficiently permeable to let water wet or pass through the implement and transfer the skin care or cleansing composition to the user. Preferably the implement material is sufficiently water insoluble so that maintains its integrity until the skin care or cleansing composition is substantially used up. Useful materials include polymeric mesh, woven or nonwoven fabric, paper, tissue, sponge or laminate of foam and fabric. Advantageously a nonwoven fabric or light weight polymeric meshed substrate may be used. A useful material is an extruded tubular netting mesh, particularly prepared from polyolefins such as polyethylene and the like, and other materials such as polyamides or polyesters and the like. They may be single or multiple ply netting such as in a pouf. The mesh structure may be polygonal, such as diamond shaped, or the like. Also suitable are irregular shapes. Advantageously the implement cells are open and that preferably the contents within the implement are observable from the exterior.

Optionally sponge like materials may also be included in the implement. Useful sponge materials are closed cell materials either of synthetic or natural origin. Synthetic sponges are advantageously formed of foamed polyurethane and the like. Optionally the sponge material may be shaped to resemble an aesthetic form or be adapted to hold a water soluble or dispersible pouch or dispensing device containing the skin care or cleansing composition.

The inventive personal care article advantageously contains a water insoluble substrate as a component. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable water insoluble substrates which meet the above criteria include The substrate may for example be a woven or nonwoven fabric, paper, tissue, sponge or laminate of foam and fabric. Water insoluble substrates can also be described as fibrous structures/assemblies. Fibrous structures/assemblies described herein is comprised of synthetic and natural fibers converted via conventional, well-known nonwoven, woven or knit processing systems or combinations thereof into fibrous structures/assemblies. Generally well known nonwoven processing systems transform fibers and filaments directly into cohesive structures with adequate strength that are not manufactured via knitting or weaving. Synthetic fibers described herein include but are not limited to polyethylene, polypropylene, polyester, viscose rayon, polylactic acid and nylon and any blends/combinations thereof. Non-limiting examples of synthetic materials useful as components in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like; polyesters such as Fortrel®, Kodel®, and the polyethylene terephthalate fibers, Dacron®; polyolefins such as polypropylene, polyethylene; polyvinyl acetate fibers and mixtures thereof. Non-limiting examples of natural materials useful as components in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided. Additionally synthetic fibers used herein can be described as staple and continues filaments including any blend thereof. Additionally fibers used herein include multi-component fibers or combinations thereof. Fiber deniers included herein range form 1.0 denier to 9.0 denier including any combinations thereof. Fibers are separated oriented and deposited on a forming or conveying surface. Methods used to arrange or manipulate fibers described herein into a fibrous assembly included but are not limited to carding/garnetting, airlay, wetlay, spunbond, meltblown are any combination/iteration thereof. Cohesion, strength and stability are imparted into fibrous assembly via bonding mechanism that include but are not limited to needlepunching, stitch bonding, hydroentangling, chemical bonding and thermal bonding and any combination/iteration thereof. Webs formed range in basis weight from 25 g/m^2 to 750 g/m^2. Fibers that comprise fibrous structure/assembly may also be used that are not mechanically, chemically, and thermally bonded to one another. Such structures that form a plurality of fiber to fiber contacts all well suited for the present invention.

Non-woven substrates made from synthetic material useful in the present invention can also be obtained from a wide variety of commercial sources, such as e.g. Sontaro® 8868, a hydro-entangled material, containing about 50% cellulose and about 50% polyester, and having a basis weight of about 60 gsy or 2.2 oz per sq. yard, having rectangular apertures of about 1.5 mm by 2 mm in dimension with about 150 to 160 apertures per sq. inch, available from Dupont Chemical Corp; PGI Laveft fabric, a 2.35 oz/sq. yd., 63% rayon/29% PET/8% binder fabric with rectangular apertures of about 2 mm×3 mm in dimension having about 40 to 45 apertures per square inch from PGI Corporation; Carlee high loft fabric, 2.0 oz/sq.yd., 100% polyester fabric from Carlee Corporation; and KC 5A high loft fabric, approx. 2.5 oz per sq. yard, 100% polyester fabric from Kimberly Clark Corporation.

Most preferred as a component substrate for purposes of this invention are Fibrous structures/assemblies, especially blends of rayon/polyester and ratios of 10:90 to 90:10, preferably ratios of 20:80 to 80:20, optimally 40:60 to 60:40 by weight. Anywhere from 1 to 100, preferably from 5 to 50 single wipe implements may be stored within a dispensing implement or container, preferably a moisture impermeable implement or container. During storage and between dispensing, the container is preferably resealable. Single wipe containing implements may also be employed.

Apertured Fabrics

The inventive skin care or cleansing implement may optionally include at least one apertured layer, where a pattern is created by a network of bundled fiber segments surrounding apertures or holes; or in a contiguous nonwoven web which has been apertured or provided with slits or other openings. In one preferred embodiment, the water insoluble material is a substantially contiguous network of water insoluble fibers having a plurality of macroscopic openings. A macroscopic opening is defined as an opening that is large relative to the intrinsic pore size of the water insoluble material. In a typical spunbond or bonded carded web, for example, a macroscopic opening would appear to the eye to be a deliberately introduced hole or void in the web rather than a characteristic pore between adjacent fibers, and specifically could have a characteristic width or major axis diameter of about 0.1 mm to about 10 mm, or larger; preferably about 1 mm to about 5 mm. A useful characteristic width may be defined as 4 times the area of the aperture divided by the perimeter. Useful fabric aperture densities are about 10 to 700 per square inch, preferably about 20 to 500 per square inch.

The water insoluble substrates or fabrics of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different permanent colors as distinguished from the variable indicator contained in the implement, thereby helping the user to further distinguish the surfaces.

The apertured fabric or sheet may be bonded to at least one other nonwoven sheet of water insoluble fibers ("second sheet") by lamination, adhesives, stitching, fasteners, or other art recognized binding methods. Preferably, the second sheet is attached to the apertured sheet by means of lamination, adhesives and related agents, including hot melts, latexes, glues, starch, waxes, and the like, which adhere or join the upper regions of the apertured sheet with adjacent portions of the second sheet. Preferably, adhesives are applied only to the most elevated portions of the apertured sheet to effect the bonding between the apertured sheet and the second sheet, leaving the apertures substantially free of adhesive. Adhesive application can be through meltblown application of hot melt glues and thermoplastic materials, spray or swirl nozzles of melted or dissolved adhesives, printing of adhesive material onto one or both surfaces before joining, and the like. If adhesives are applied directly to the apertured sheet by means of spray, mist, aerosol, or droplets in any form, prior to contact of the apertured sheet with the water insoluble matter, then it is desirable to use a template or patterned shield to prevent application of adhesive to the apertures to avoid clogging. Preferably, the second sheet is composed of polyester or a polyester and cellulose blend, does not contain apertures and has the characteristics of high loft, a basis weight of about 1 to 5 ounces per square yard, preferably about 2 to 3 ounces per square yard and optionally contains a binder. Useful binders include latex or acrylic materials added to the fabric between about 5 to 40 weight percent of the fabrics total weight, preferably between about 5 to 25 weight percent.

Reactive and Anhydrous Chemistry Configurations

Useful chemistry configurations suitable for use with the inventive implement include a cosmetic composition with suspended insolubilized surfactants in a solidified matrix or a substantially nonaqueous liquid carrier. Other useful chemistry systems may include effervescent cosmetic compositions, bleaching systems, or any system that may react with each other or with water and that are compatible with the other constituents of the inventive product.

Effervescent cosmetic compositions with particular ratios of different organic acids for different sensory effects which e.g. vary with water solubility such as citric, malic, tartaric, and fumaric acids combined with carbonate or bicarbonate salts where at least one of the acid or of the carbonate/bicarbonate salt is in the discontinuous phase may be used.

Bleaching systems may be used that contain anhydrous sodium perborate and/or sodium percarbonate and the like. These materials are hydrogen peroxide donors when in contact with water—preferably where the a pH is greater than about 8.0.

Depilatory systems may be used that contain a precursor acid that reacts with the base when the formulation is hydrated to form the active material for removing hair from the body. These acids may include such as thiolactic acid, thioglycolic acid and other aliphatic mercapto acids and the like. These materials may be activated by ingredient(s) within the dispersed phase (such as one or more alkaline materials or precursor(s) thereof), within the continuous phase, within both phases or by a component added to the inventive composition during product use such as water or encapsulated ingredient(s) liberated during product use such as by rubbing or by two packaging chambers which during use can be broken to allow for mixing of the two phases (such as water and the inventive composition).

Other useful additions to the inventive implement include materials with exothermic heats of solution or dispersion in water (such as zeolites and the like) or materials with endothermic heats of solution or dispersion in water (such as ammonium chloride, and the like). Carbon dioxide encapsulated by any suitable solid water soluble or dispersible material such as starch or sugar or blends thereof (such as Pop Rocks™, or chemicals that react to change color upon contact with water or with each other when solvated with water such as any water soluble or dispersible colorant e.g. blue 1, yellow 5 or 10, green 3, 5, or 7; blends thereof and the like.

The inventive implement may also include reactive ingredients which are structured with waxes, polymers, etc. to form solid forms. The inventive cosmetic compositions may also contain an oil, an emulsifier, an organoclay, and 10% or more dispersed solids by weight, or may contain materials that impart a cooling sensation on the skin such as menthol and derivatives and the like.

Structurants and Stabilizers

Compositions suitable for use with the implement according to the invention may also include in-use water structurants (such as lauric acid and trihydroxystearin); and stabilizers such as self-orienting/structuring organophilic particles which impart rheological elasticity (yield stress) such as organically modified clays (chemically reacted with fatty quaternium compounds for hydrophobicity) based on Hectorite, Bentonite, or synthetic clays such as Hydrotalcite that are available from Rheox/Elementis (Hightstown, N.J.), Southern Clay (Gonzales, Tex.), and SUD Chemie (Munich, Germany) respectively. Other useful components include elastomers such as those with silicone or nonsilicone backbones with different crosslinking groups, such as phenylated and polyvinyl crosslink linkages and the like. Specific useful elastomers include DC 9040 available from Dow Corning (Midland, Mich.), GE SFE818 available from General Electric (Waterford, N.Y.), Belsil RG 100 available from Wacker (Munich, Germany), and KSG 21 available from ShinEtsu (Tokyo, Japan). Such elastomers can act as stabilizers for the inventive composition.

Filler or oil absorbing particulates which are insoluble in the continuous phase may be advantageously used. Useful materials in this category include ultra-fine materials such as mica, talc, titanium dioxide, silica and starch. Finely powdered silicone polymers such as KSP 100 available from ShinEtsu may be used. Hollow and/or low density materials such as starch spheres (e.g. Natrasorb-W) available from National Starch (Bridgewater, N.J.), polymeric spheres (e.g. Expancel available from Akzo Nobel (Duluth, Ga.); and borosilicate glass spheres (e.g. Luxsil available from PQ corporation (Philadelphia, Pa.). These materials can act as stabilizers for the inventive composition.

Hydrophobic polymeric gellants may be used to adjust the viscosity of the continuous phase. Useful materials include Krayton Gel (e.g. Krayton D-1101 available from Krayton Polymers Corporation (Houston, Tex.); Hydrophobized PVP copolymers (e.g. Ganex series available from ISP Products Inc. (Wayne, N.J.); Silicone polymers (e.g. DC 2-1491) available from Dow Corning (Midland, Mich.), Acrylate polymers/copolymers (e.g. poly(sodium acrylate)) available from Rohm & Haas company (Philadelphia, Pa.); and Silicone-acrylate polymers(e.g. SA 70, VS 70, and VS80 available from 3M company (St. Paul, Minn.). These materials can also act as stabilizers for the inventive composition.

Crystalline hydroxyl-containing stabilizers including ethoxylated fatty alcohols (e.g. Neodol from Shell (Houston, Tex.) and trihydroxystearin (e.g. Thixcin-R from Rheox (Hightstown, N.J.) may be advantageously used.

Waxy materials such as organic waxes; silicone waxes. silicone-acrylate waxes, fatty amides may be useful in the inventive composition. Other useful components include high melt point hydrocarbons (e.g. having a melting point of greater than 55 C such as petrolatum. These materials can also act as stabilizers for the inventive composition.

Polymers that form water gels and travel to emulsion interfaces upon contact with water are also useful as stabilizers in the inventive composition such as Pemulen® (high molecular weight, cross linked copolymers of acrylic acid and a hydrophobic comonomer) and Carbopol® (high molecular weight homo- and copolymers of acrylic acid, optionally crosslinked with various substituents such as polyalkenyl polyethers) available from Noveon Chemicals (Cleveland, Ohio) and the like; Glyceril Polyacrylates (e.g. Lubrajel series from ISP (Wayne, N.J.)).

Surfactants

Soaps

The inventive product may contain a soap in its continuous or discontinuous phase. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. The soaps useful herein are the well known alkali metal salts of alkanoic or alkenoic acids having about 8 to 50 carbon atoms, preferably about 12 to about 22 carbon atoms. They may also be described as alkali metal carboxylates of alkyl or alkene hydrocarbons having about 12 to about 22 carbon atoms.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Anionic Surfactants

One or both of the continuous or discontinuous phases may also contain non-soap anionic surfactants. The anionic surfactant (which may comprise about 3 to 40% by wt. of both phases; 3 to 40% in the continuous phase and 3 to 40% in the discontinuous phase) may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$-$C_{18}$ alkyl sulfate) or alkyl ether sulfate (including alkyl glyceryl ether sulfates), and the like. Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates, and the like.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula RCON($CH_3$)$CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic Acid" issued Feb. 28, 1995 to Ilardi et al., hereby incorporated by reference into the subject application. This compound has the general formula:

$$RC\overset{O}{\overset{\|}{-}}O-\overset{X}{\overset{|}{C}H}-CH_2-(OC\overset{Y}{\overset{|}{H}}-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Zwitterionic and Amphoteric Surfactants

One or both of the continuous or discontinuous phases may also contain zwitterionic/amphoteric surfactants. Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

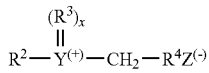

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P, P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

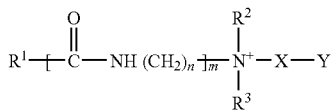

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

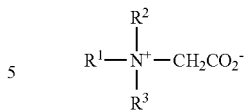

and amido betaines of formula:

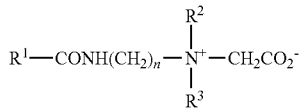

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

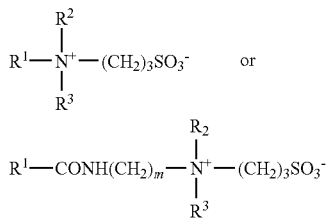

where m is 2 or 3, or variants of these in which $-(CH_2)_3SO^-_3$ is replaced by

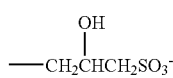

In these formulae $R^1$, $R^2$ and $R^3$ are as discussed previously.

Amphoacetates and diamphoacetates are also intended to be covered in possible zwitterionic and/or amphoteric compounds which may be used, especially C8-C20 amphoacetates or mixtures thereof, and the like. A suitable amphoacetate is sodium laurylamphoacetate.

The amphoteric/zwitterionic surfactant, when used, generally comprises about 2 to 30%, preferably about 3 to 20% by weight, more preferably about 3 to 10% of the composition. 2 to 30% in the continuous phase and 1 to 5% in the discontinuous phase).

A preferred surfactant system of the invention comprises the following: anionic surfactant (e.g. alkali metal alkyl ethersulfate), about 2-50%; amphoteric surfactant (e.g. alkyl betaine or alkyl amphoacetate), about 3-20% based on the total composition.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in Patent No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-and/or 6-position, preferably predominantly the 2-position.

The nonionic comprises about 0 to 40% by wt. in each phase of the composition, preferably about 0 to 15% by wt. 0 to 40% in the continuous phase and 0 to 20% in the discontinuous phase).

Occlusive Emollients

One way of moisturizing is to reduce the rate of water loss from the stratum corneum (skin surface) by depositing an occlusive emollient on the skin surface which prevents water evaporation. Another technique is to add hygroscopic nonocclusive substances (humectants), which will retain water to the stratum corneum, making water available to the skin surface thereby producing the desired cosmetic effect. Nonocclusive emollients also function by improving the lubricity of the skin. Both occlusive and nonocclusive emollients as well as mixtures thereof are operative in the present invention and may be present in either or both the continuous or discontinuous phases. Examples of occlusive emollients include, lanolin and its derivatives, long chain esters, waxes, saturated and unsaturated fatty alcohols, conditioning oils and extracts, phospholipids, sterols, ceramides and silicones. The following occlusive emollients may optionally be found in the compositions of the invention.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of occlusive emollients include mineral oil, petrolatum, silicone oil such as dimethyl polysiloxane, lauryl and myristyl lactate, fatty acid oils, triglycerides, and the like.

The occlusive emollient is generally used in an amount from about 0 to 70%, preferably about 5 to 40% by wt. of the phase in which it is found in. Generally, it should comprise no more than 70% of such phase. A portion of the emollient may be present in the form of solid or semi-solid beads. The beads are optionally used in an amount from about 0.05 to 5% by wt.

Nonocclusive Emollients

Some examples of nonocclusive emollients are liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol e.g., Solulan-75). Some other preferred moisturizers are the nonoclusive liquid water soluble polyols and the essential amino acid compounds found naturally in the skin. Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA. Other examples of both types occlusive and nonocclusive emollients are disclosed in "Emollients—a Critical Evaluation," by J. Mausner Cosmetics & Toiletries, May 1981, incorporated herein by reference.

In addition, the continuous or discontinuous phases of the compositions of the invention may include optional ingredients as follows:

Sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4, 2'4' trichlorodiphenylether (DP300), quaternary ammonium compounds; preservatives such as dimethyloldimethylhydantoin (Glydant XL1000), parabens, sorbic acid etc.

The compositions may also comprise coconut acyl mono- or diethanol amides and the like as suds boosters.

Antioxidants such as, for example, butylated hydroxytoluene (BHT) may be used advantageously in amounts of about 0.01% or higher if appropriate.

Cationic conditioners which may be used include Polyquaternium-10, Quatrisoft LM-200, Polyquaternium-24, Merquat Plus 3330, Polyquaternium 39, Ucare polymer JR-400, Jaguar® type conditioners and the like.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sep. 15, 1992 to Montague, hereby incorporated by reference.

Other ingredients which may be included are exfoliants such as polyoxyethylene beads, silica particles, walnut shells and apricot seeds, and the like. pH and viscosity adjusters may be optionally used to e.g. adjust the pH of the separate phases prior to being combined into the inventive product. Such suitable pH adjusters may include citric acid, glycolic acid, lactic acid, other alpha or beta hydroxy acids, and the like.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLE 1

An inventive cleansing implement having a substantially anhydrous composition according to table 1 having a hydrophilic continuous phase may be prepared. A combination of anionic and amphoteric surfactants were added to each phase. The composition is useful as a shampoo and for oily skin cleansing. The composition may either be coated on a nonwoven substrate or be added to a flexible spongeform body having a density of 0.035 g/cm$^3$ in a concentration greater than 15% by wt. based on the substrate. The nonwoven substrate may have the following properties:

| Property | Value |
| --- | --- |
| Basis Weight (g/m$^2$) | 65 |
| Fiber Composition | 70% PET/30% Rayon |

Optionally about 1.0 to 6.0 grams are placed in a water soluble or dispersible polyvinyl acetate implement or an implement comprised of another water soluble or dispersible material such as starch, sugar, other polymers or blends thereof. The implement is then sealed and placed in to a pouch of a 5 cm by 8 cm implement where the walls of the implement are formed by heat sealing the entire circumference or partial circumference of two or more non-woven spun lace webs. Spun laced webs may be comprised of a barrier substrate such as spunbond/meltblown/meltblown/spunbond (SMMS) web. The web may be a single meltblown layer but preferably it is a combination of several layers such as the four layers described above or three layers of spunbond/meltblown/spunbond (SMS).

TABLE 1

| Component | Concentration (w/w) |
| --- | --- |
| Water Soluble Anhydrous Fluid [1] | 25% |
| Non Polar Oil [2] | 5% |
| Ethoxylated Fatty Alcohol | 5% |
| Emollient Ester | 4% |
| Fatty Amide | 1% |
| Hydrocarbon/Silicone Wax [3] | 2% |
| Glyceryl Polyacrylate | 10% |
| Anhydrous Suspended or Solubilzed Anionic Surfactant Powder | 12% |
| Anhydrous Suspended or Solubilized Amphoteric Surfactant Powder | 2% |
| Hydrophilic Structuring Polymer [4] | 2% |
| Sodium Bicarbonate | 15% |
| Citric Acid | 15% |
| Fragrance | 2% |
| TOTAL | 100% |

[1] such as propylene glycol or glycerine
[2] such as polyisobutene
[3] such as paraffin or ShinEtsu KP 100 silicone acrylate wax
[4] such as pemulen ™ or carbopol ™

EXAMPLE 2

An inventive implement releasably containing a lotion composition according to table 2 may be prepared using an implement substrate as described in Example 1.

TABLE 2

| Components | Concentration (w/w) |
| --- | --- |
| Non-Polar Oil | 30% |
| Ethoxylated Fatty Alcohol | 5% |
| Emollient Ester[5] | 5% |
| Fatty Amide [6] | 2% |
| Organic/Silicone Wax | 3% |
| Liquid Emulsifier [7] | 5% |
| Suspended water gellant [8] | 2% |
| Organic modified clay [9] | 10% |
| Hydrophobic Polymeric Structurant [10] | 3% |
| Sodium Bicarbonate | 15% |
| Citric Acid | 15% |
| Fragrance | 5% |
| TOTAL | 100% |

[5] such as isopropyl myristate
[6] such as glyceryl stearamide
[7] such as Brij 93 Veg ™ from Unichema
[8] such as pemulen ™ or carbopol ™
[9] such as Bentone ™ 38 V from Rheox
[10] such as Krayton ™ gel

EXAMPLE 3

An inventive implement releasably containing a moisturizing cleansing composition having color changing properties when blended with water according to table 3 may be prepared using an implement substrate as described in Example 1.

TABLE 3

| Components | Concentration (w/w) |
|---|---|
| Sunflower Seed Oil | 27.99% |
| Neodol ™ 45 (ethoxylated fatty alcohol) | 10% |
| Bentone ™ 38 ISD GEL (Organoclay) | 15% |
| Tauranol ™ I78 (Sodium Cococoyl Isethionate Powder) | 10% |
| Brij 93 Vej ™ | 5% |
| Sodium Bicarbonate | 15% |
| Citric Acid | 15% |
| Green #3 | 0.01% |
| Fragrance | 2% |
| TOTAL | 100% |

EXAMPLE 4

An inventive implement releasably containing a wash-off moisturizing composition according to table 4 may be prepared using an implement substrate as described in Example 1.

TABLE 4

| Components | Concentration (w/w) |
|---|---|
| Sunflower Seed Oil | 45% |
| Bentone ™ 38 ISD GEL (Organoclay) | 15% |
| Tauranol ™ 178 (Sodium Cocoyl Isethionate Powder) | 1% |
| Brij 93 Vej ™ | 9% |
| Sodium Bicarbonate | 12.5% |
| Citric Acid | 12.5% |
| Fragrance | 5% |
| TOTAL | 100% |

EXAMPLE 5

An inventive implement releasably containing a moisturizing cleansing and conditioning composition according to table 5 may be prepared using an implement substrate as described in Example 1.

TABLE 5

| Components | Concentration (w/w) |
|---|---|
| Non-Polar Oil | 20% |
| Fatty Alcohol | 4% |
| Ethoxylated Fatty Alcohol | 6% |
| Emolient Ester | 5% |
| Fatty Amide | 2% |
| Organic/Silicone Wax | 3% |
| Anhydrous Suspended Anionic Surfactant Powder | 8% |
| Anhydrous Suspended Amphoteric Surfactant Powder | 2% |
| Organic Clay | 15% |
| Hydrophobic Polymeric Structurant | 3% |
| Sodium Bicarbonate | 15% |
| Citric Acid | 15% |
| Fragrance | 2% |
| TOTAL | 100% |

EXAMPLE 6

An inventive implement releasably containing a lotion composition according to table 6 may be prepared using an implement substrate as described in Example 1.

TABLE 6

| Components | Concentration (w/w) |
|---|---|
| Sunflower Seed Oil | 45% |
| Bentone ™ 38 ISD GEL (Organoclay) | 15% |
| Brij 93 Vej ™ | 5% |
| Sodium Bicarbonate | 15% |
| Citric Acid | 15% |
| Fragrance | 5% |
| TOTAL | 100% |

EXAMPLE 7

An inventive implement releasably containing a water-activated hair bleaching composition according to table 7 may be prepared using an implement substrate as described in Example 1.

TABLE 7

| Components | Concentration (w/w) |
|---|---|
| Sunflower Seed Oil | 35% |
| Bentone ™ 38 ISD GEL (Organoclay) | 15% |
| Brij 93 Vej ™ | 5% |
| Neodol ™ 45 (Ethoxylated Fatty Alcohol) | 20% |
| Sodium Perborate | 15% |
| Sodium Carbonate | 5% |
| Fragrance | 5% |
| TOTAL | 100% |

EXAMPLE 8

An inventive implement releasably containing a solid water-activated cleansing and conditioning composition according to table 8 may be prepared using an implement substrate as described in Example 1.

TABLE 8

| Components | Concentration (w/w) |
|---|---|
| Non-Polar Oil | 10% |
| Fatty Alcohol | 4% |
| Ethoxylated Fatty Alcohol | 6% |
| Emolient Ester | 5% |
| Organic/Silicone Wax | 25% |
| Anhydrous Suspended Anionic Surfactant Powder | 8% |
| Anhydrous Suspended Amphoteric Surfactant Powder | 2% |
| Organic Clay | 15% |
| Hydrophobic Polymeric Structurant | 3% |
| Sodium Bicarbonate | 10% |
| Citric Acid | 10% |
| Fragrance | 2% |
| TOTAL | 100% |

EXAMPLE 9

An inventive implement releasably containing a water-activated depilatory composition according to table 9 may be prepared using an implement substrate as described in Example 1.

TABLE 9

| Components | Concentration (w/w) |
|---|---|
| Sunflower Seed Oil | 29.5% |
| Bentone 38 ISD GEL (Organoclay) | 15% |
| Brij 93 Vej | 5% |
| Neodol 45 (Ethoxylated Fatty Alcohol) | 20% |
| Thiolactic Acid (Powder) | 13% |
| Sodium Bicarbonate | 5% |
| Calcium Hydroxide (Fine Powder) | 12%* |
| Fragrance | 0.5% |
| TOTAL | 100% |

*Calcium Hydroxide is used at a level sufficient to provide a pH of 10.5 to 12.5 in a saturated aqueous solution of the depilatory composition.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A personal care implement, comprising:
   a. a water insoluble substrate, the substrate affixed to a membrane barrier;
   b. the membrane barrier being water soluble or dispersible and defining a chamber;
   c. the chamber containing a composition including a dispersed phase and a continuous phase;
   d. the dispersed phase including a first component, the first component being capable of chemically reacting with a second component that is different from the first;
   e. the continuous phase present in the composition is composed of a substantially anhydrous carrier;
   f. at least one stabilizer contained in the dispersed phase wherein the stabilizer is selected from an organophilic particle;
   g. wherein the first component is substantially unsolvated in the carrier;
   h. an anionic surfactant in a concentration of at least about 2% by wt. based on the composition when the at least one stabilizer consists solely of waxy particles, amphipathic compounds or polymers, or a combination thereof; and
   i. wherein the first and second components do not substantially react with water or each other until dispersed or dissolved in water at during cleansing and skin treatment by a consumer.

2. The implement of claim 1 wherein the dispersed phase comprises the first and the second components and wherein the second component is substantially unsolvated in the carrier.

3. The implement of claim 1 wherein the reaction of the first component with water or the first component and the second component is not polymerization.

4. The implement of claim 1 wherein the at least one reactive component has a particle size range of about 0.5 to 5000 μ.

5. The implement of claim 1 wherein the stabilizer is an organophilic particle in the particle size range of about 0.02 to 250 μ.

6. The implement of claim 5 wherein the organophilic particle is selected from a waxy particle, organophilic silica, organophilic clay, or blends thereof.

7. The implement of claim 1 wherein the carrier may contain components that are polar, nonpolar or a blend thereof.

8. The implement of claim 1 further comprising dispersed surfactants that are substantially unsolvated by the carrier.

9. The implement of claim 1 further comprising structuring agents that form lamellar, hexagonal, or cubic surfactant phases upon contact with water at 25 C.

10. The implement of claim 1 wherein the first component is capable of producing a gas in aqueous solution when reacted with an acid and the second component is an acid or forms an acid in the presence of water.

11. The implement of claim 1 wherein the first component is capable of generating a peroxide compound when dissolved in water.

12. The implement of claim 1 wherein the first component is capable of generating sulfide ions when reacted with an alkaline material and water.

13. The implement of claim 1 wherein the carrier contains an oil, an emulsifier and wherein the stabilizer is an organophilic clay; and the composition contains a total of at least about 10% of reactive dispersed solids by wt based on the composition.

14. The implement of claim 1 where the first component is a solid or semisolid containing dissolved carbon dioxide.

15. The implement of claim 1 wherein the water insoluble substrate includes at least one layer of a woven or non-woven hydophilic fabric.

16. The implement of claim 15 wherein the hydrophilic fabric is a blend of cellulosic and non-cellulosic fibers.

17. The implement of claim 15 wherein the hydrophilic fabric comprises rayon and polyester.

18. The implement of claim 15 wherein the hydrophilic fabric comprises rayon and polyester in the concentration ratio range of about 10:90 to 90:10.

19. The implement of claim 15 wherein the hydrophilic fabric contains a plurality of apertures having a major axis diameter in the range of about 0.5 to 10 mm and wherein the apertures are distributed on the substrate in the range of about 1 to 10 per linear centimeter.

20. The implement of claim 15 wherein the hydrophilic fabric comprises at least one layer of fibers made by a process selected from hydroentangled, wet laid, dry laid, spun bonded, needle punched, or air laid.

21. A method of treating the skin or hair, comprising the steps of:
   a. adding water to the implement of claim 1 and allowing the membrane to sufficiently dissolve or disperse in order to transfer a substantial portion of the composition contained in the chamber to the water insoluble substrate;
   b. contacting the skin or hair with the implement and the transferred composition;
   c. rubbing the skin or hair with the implement and the transferred composition; and
   d. rinsing off the composition from the skin.

* * * * *